United States Patent [19]

Eskelson

[11] Patent Number: 4,588,696
[45] Date of Patent: May 13, 1986

[54] PELLET PROCESS FOR THE DETECTION OF FORMALDEHYDE AND/OR GLUTARALDEHYDE

[76] Inventor: Cleamond D. Eskelson, 7402 Calle Toluca, Tucson, Ariz. 85710

[21] Appl. No.: 447,014

[22] Filed: Feb. 17, 1983

[51] Int. Cl.$^4$ ............................................. G01N 21/78
[52] U.S. Cl. ..................................... 436/130; 422/61; 436/128; 436/166
[58] Field of Search ................ 436/128, 129, 130, 95, 436/164, 166; 422/56, 61

[56] References Cited

U.S. PATENT DOCUMENTS

| | | | |
|---|---|---|---|
| 2,281,758 | 5/1942 | Galat | 436/95 |
| 2,387,244 | 10/1945 | Compton et al. | 436/95 |
| 4,295,853 | 10/1981 | Kasahara et al. | 436/66 |

OTHER PUBLICATIONS

Terada et al., Chemical Abstracts, vol. 76, 1972, No. 153642e.
Lacan et al., Chemical Abstracts, vol. 90, 1979, No. 90:136927y.
Nash et al., Biochem. J. 55:416(1953).
Eskelson et al., 1975 Pacific Conference on Chemistry and Spectroscopy, Oct. 28 through 30, 1975, North Hollywood, Ca., No. 195.

Primary Examiner—Arnold Turk
Attorney, Agent, or Firm—Cushman, Darby & Cushman

[57] ABSTRACT

A kit containing three tablets is used in a process for testing for formaldehyde and/or glutaraldehyde in a sensitive, rapid, and simple manner that is practical even when glucose is present. A first tablet containing citrus acid and glycine hydrochloride (or like buffer and strong acid, respectively) is placed in the test solution (suspected to contain formaldehyde and/or glutaraldehyde) with a tablet containing the necessary reagents for developing color. These reagents include benzoylacetone or its derivatives, and ammonium acetate. A third tablet containing effervescing material is added, causing mixing of the solution. The third tablet typically is composed of sodium hydroxide and potassium carbonate. The yellow color (if formaldehyde and/or glutaraldehyde are present) produced by the reaction is compared to colors on a color chart, and thereby the approximate amount of formaldehyde and/or glutaraldehyde present may be determined.

19 Claims, 5 Drawing Figures

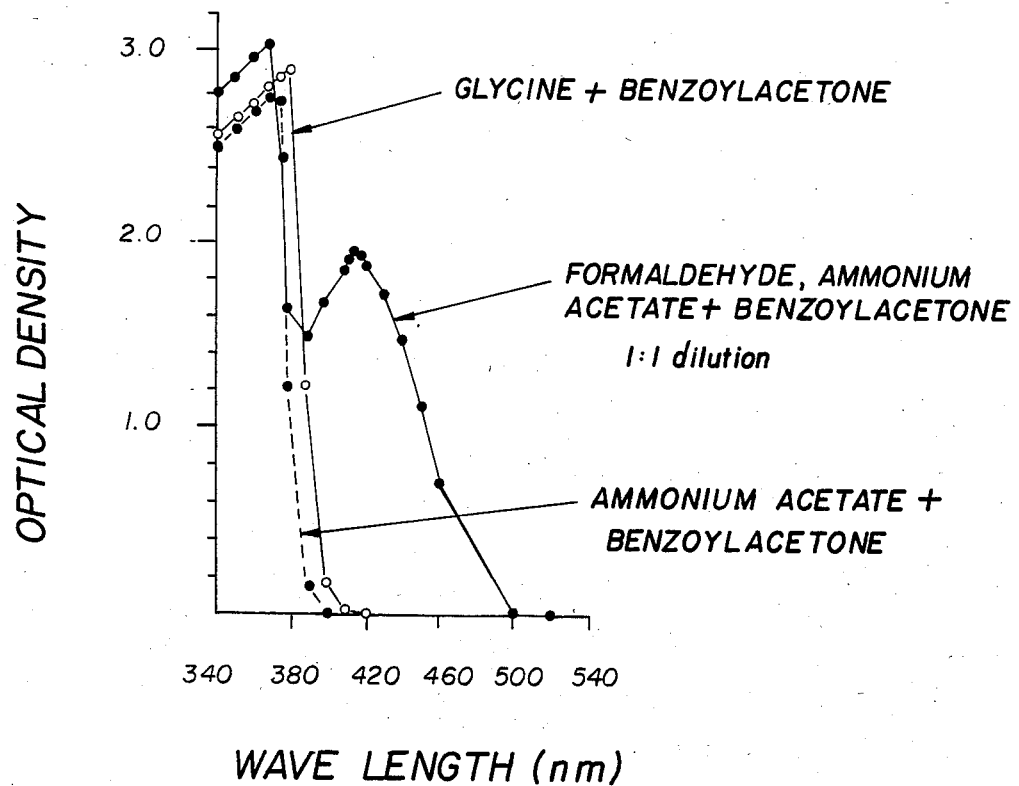
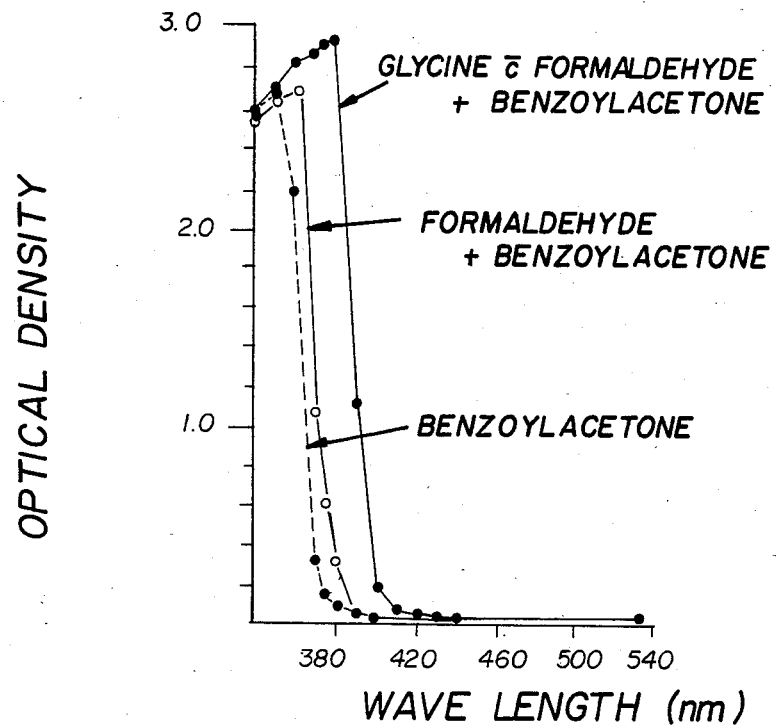

PELLET PROCESS FOR THE DETECTION OF FORMALDEHYDE AND/OR GLUTARALDEHYDE

BACKGROUND AND SUMMARY OF THE INVENTION

This invention comprises a process involving certain chemicals which are pressed into tablets. When these tablets area added to a solution containing formaldehyde and/or glutaraldehyde they rapidly cause yellow color to develop in the solution. The amount of yellow color developed is an indication of the amount of formaldehyde and/or glutaraldehyde present in the solution. The process is used to detect these aldehydes in the environment in order to help protect living systems therefrom.

The major uses for the formaldehyde test kit according to the invention are at the bed side of patients in hemodialysis centers throughout the United States. Many of the artificial kidneys (hemodialysis units) used in these centers are sterilized with formaldehyde solutions. The formaldehyde must be removed before the artificial kidneys are used for human dialysis. The major test system used for formaldehyde in these centers is the CLINITEST (trademark of Ames Laboratory), which is designed as a test for glucose and is not sensitive enough to meet the needs of the hemodialysis centers. In addition glucose is a necessary ingredient of hemodialysis solution, thus two dangers are involved, namely: formaldehyde toxicity; and the re-establishment of glucose in the hemodialysis unit after the formaldehyde is washed out and tested by the CLINITEST.

The formaldehyde test according to the invention does not detect glucose, thus the hemodialysis unit can be cleansed from its formaldehyde content using glucose containing hemodialysis solution. When the formaldehyde content as shown by using the invention is washed from the artificial kidney, it is safe for patient care without fear of inadequate amounts of glucose or excess formaldehyde amounts.

The formaldehyde detection kit and processes according to the invention utilize three tablets which are added to one ml of test (suspected formaldehyde or glutaraldehyde containing) solution. The tablets are numbered 1, 2, and 3. Tablets numbers 1 and 2 are partially dissolved in the test solution. Tablet number 3 is then added and the solution mixed thoroughly, following which the solution heats up and effervesces. After this reaction, if formaldehyde and/or glutaraldehyde are present, the solution turns yellow and is slightly cloudy. The amount of yellow color in the solution is compared to a color chart which correlates with the amount of formaldehyde present in the solution to determine actual formaldehyde content.

The most frequently used test for formaldehyde quantitation is a method described by Nash which utilizes ammonium acetate and 2, 4-pentanedione (acetylacetone). This Hantzch reaction requires a 30 minute reaction time in a hot water bath maintained at 65°-70° C., and is represented below.

REACTION OF ACETYLACETONE WITH FORMALDEHYDE AND AMMONIA

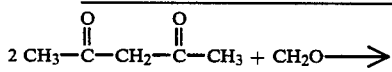

-continued
REACTION OF ACETYLACETONE WITH FORMALDEHYDE AND AMMONIA

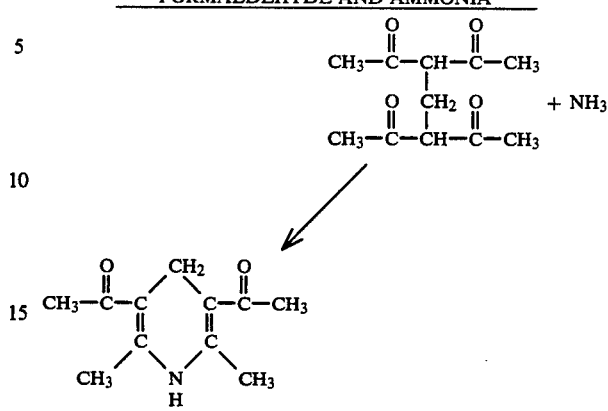

The Nash method is slow and requires laboratory equipment which is cumbersome and not readily adaptable to the bedside of a patient. In contrast to Nash, the formaldehyde detection and quantitation kit and method according to the invention are sensitive, rapid, require no laboratory equipment, and are utilizable in the presence of glucose.

It is the primary object of the present invention to provide a sensitive, rapid, versatile, and simple test, and kit for performing the test, for formaldehyde and/or glutaraldehyde. This and other objects of the invention will become clear from an inspection of the detailed description of the invention and the appended claims.

BRIEF DESCRIPTION OF DRAWINGS

FIG. 4 is a graphical representation of the absorption spectrum of various components of a formaldehyde reaction mixture; and FIG. 5 is a graphical representation of the absorption spectrum of various other components of formaldehyde reaction mixture, illustrating—like FIG. 4—the shift to longer wave lengths when various chemicals contained in the kit tablets according to the invention are added to benzoylacetone.

DETAILED DESCRIPTION

According to the present invention a kit is provided for testing of formaldehyde and/or glutaraldehyde. The kit preferably comprises three tablets.

The first tablet of the kit according to the invention is typically composed of a buffer and a strong acid. An exemplary useful specific embodiment comprises a tablet composed of 19:2.8 parts of citric acid (the buffer) to glycine hydrochloride (the strong acid), respectively. The first tablet typically would weight about 450 mg.

The second tablet of an exemplary kit according to the present invention includes benzoylacetone or its derivatives (i.e. amine, chloride, bromide, iodide, fluoride, nitrate, methyl, and/or alkyl and phenyl groups as well as alkene and alkyne derivatives) as a color reagent for the actual detection of formaldehyde and/or glutaraldehyde. The benzoylacetone is normally a powder and thus can readily be pressed into pills. This is in contra-distinction to acetylacetone, which is normally a liquid. The second tablet also includes ammonium acetate. A preferred ratio of components is 5:0.040 parts of ammonium acetone to benzoylacetone, respectively. The second tablet typically would weigh 127 mg.

The third tablet of the kit according to the invention comprises an effervescent material which, when contacted by the test solution containing the dissolved first and second tablets, causes efective mixing of the components so that a generally homogenous solution produced. Typically the third tablet would be composed of 14.5 parts of sodium hydroxide to potassium carbonate, respectively, and typically could have a weight of 220 mg.

Figure 3:
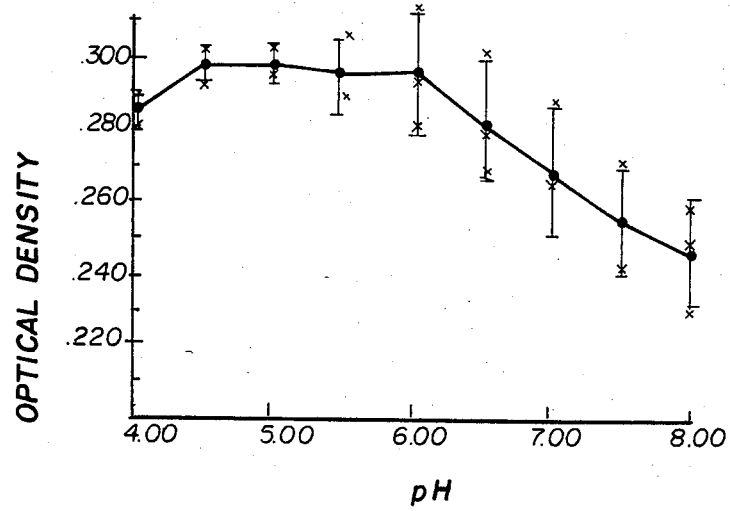
FIG. 3 is a graphical representation of the effect of pH on color development with the formaldehyde reaction mixture.

The first and third tablets are important for developing heat in the reaction mixture (by a neutralization reaction) which is necessary for color development of formaldehyde at low concentrations. Additionally, the first and third tablets develop and maintain the pH of the reaction mixture at about 4.5-6. FIG. 3 illustrates the desirability of maintaining the pH in that range.

Using the asymetric compound, benzoylacetone and the reaction scheme of Scholtz and others, three reaction products would be expected (3 isomers of dihydrolutidine) from the condensation of formaldehyde with benzoylacetone, and three reaction products would be expected from the reaction of ammonium with the two condensation products. This may be represented as follows:

REACTION OF BENZOYLACETONE WITH
FORMALDEHYDE AND AMMONIA

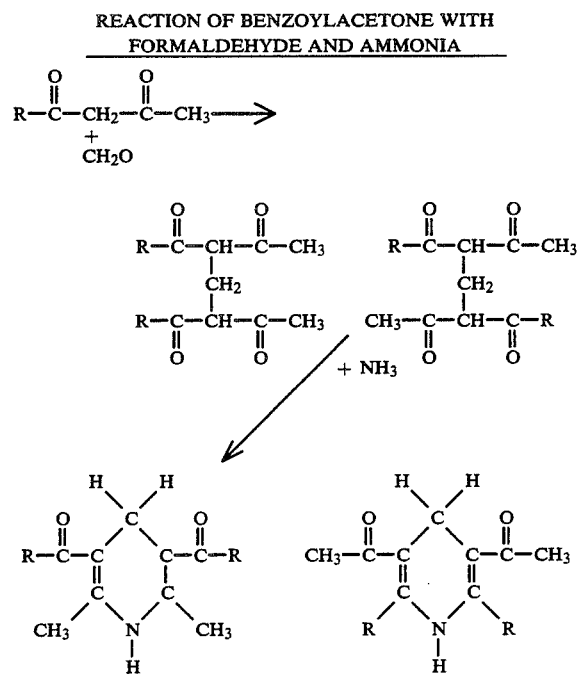

-continued
REACTION OF BENZOYLACETONE WITH
FORMALDEHYDE AND AMMONIA

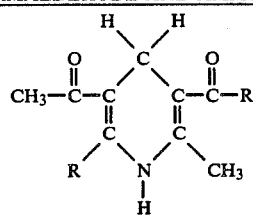

The reaction with benzoylacetone probably involves the condensation of formaldehyde with the beta diketone and the condensation of ammonia to form dihydrolutidines. Evidence for a step wise reaction is suggested in the absorption spectrum in FIGS. 4 and 5 in which benzoylacetone solution is placed in the presence of only formaldehyde or ammonium acetate or glycine or glycine plus formaldehyde or ammonium acetate plus formaldehyde; compared to that of benzoylacetone solution alone. The absorption spectrum was shifted to longer wave length compared to benzoylacetone along or when formaldehyde, ammonium acetate, or glycine was added to benzoylacetone; this suggests reactions or weak associations were occurring with these compounds and benzoylacetone. This fits the suggestions made by Nash, and others, that the reaction occurs in two stages. The single reactants, formaldehyde, benzoylacetone, shifted the absorption spectrum least and that of glycine and benzoylacetone, shifted the absorption spectrum next to the greatest. This was not caused by the decrease in pH due to glycine hydrochloride. When formaldehyde was added to the glycine-benzoylacetone mixture only a small shift in absorption spectrum was noted (again see FIGS. 4 and 5). This suggests that the second phase, the condensation of the formaldehyde with the glycine-benzoylacetone association product, did not occur in this mixture, or if the three reactants did combine no color compound developed. When formaldehyde was added to the ammonium acetate and the benzoylacetone, a maximum absorption peak occurred at 416-418 nm (see FIG. 4). Because the benzoylacetone absorption spectrum is zero at 400 nm, the color reagent, benzoylacetone, does not interfere with the colorimetric determination of formaldehyde (see FIG. 5).

Ammonium acetate is the only ammonium salt tested which functions satisfactorily under these conditions. Ammonium phosphates, ammonium chloride and ammonium citrate have all been tested but none result in the sensitivity approaching that of ammonium acetate.

Figure 1:
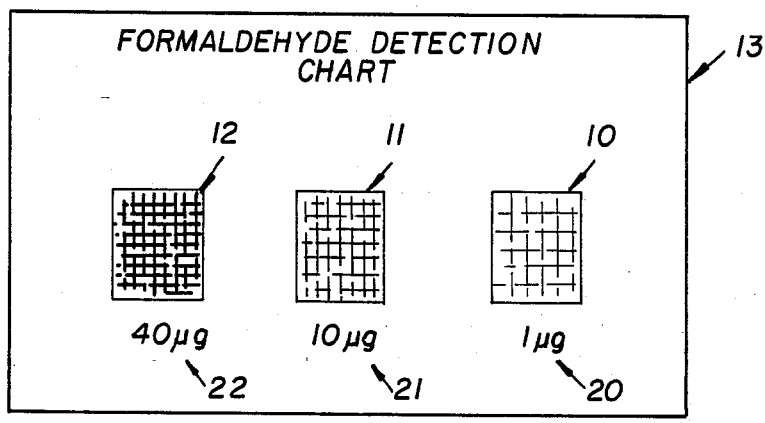
FIG. 1 is an illustration of a formaldehyde detection chart according to the invention showing different intensities of yellow color corresponding to different formaldehyde concentrations in the test solution being studied.
Figure 2:
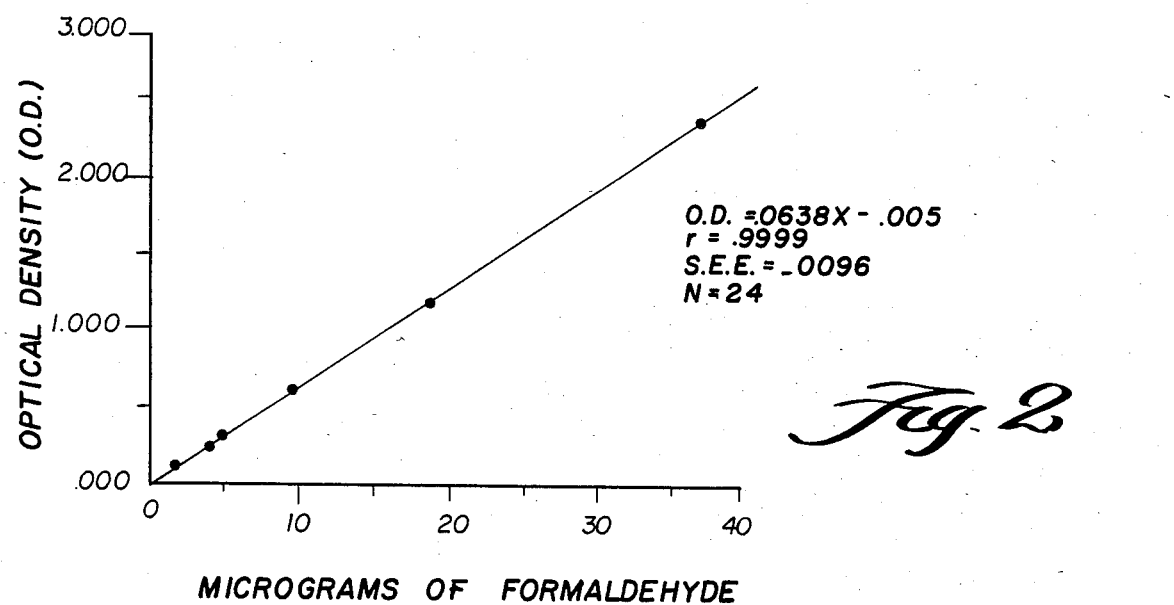
FIG. 2 is a graphical representation of a standard curve for formaldehyde using benzoylacetone as a color reagent.

In an exemplary practice of a method according to the present invention, the first and second tablets are partially dissolved in the test solution (i.e. the solution suspected to have formaldehyde and/or glutaraldehyde). Then the third tablet is added, and the solution mixed thoroughly. During this mixing the solution heats up an effervesces, and if formaldehyde and/or glutaraldehyde are present a strong yellow color is produced. The intensity of the yellow color depends upon the amount of formaldehyde and/or glutaraldehyde present, as can be seen from FIG. 2. The yellow color produced is compared to the various yellow color blotches 10, 11, or 12 (etc.) on the chart 13, and by this comparison the approximate amount of formaldehyde in the test solution can be determined. Note that each color blotch 10-12 has indicia 20-22 associated therewith which relates the concentration of formaldehyde to the strength of the yellow color.

According to the present invention it is possible to detect formaldehyde down to a level of about 0.2 parts per million in less than two minutes (e.g. 1.25-2 minutes).

While the invention has been herein shown and described in what is presently conceived to be the most practical and preferred embodiment thereof, it will be apparent to those of ordinary skill in the art that many modifications may be made thereof within the scope of the invention, which scope is to be accorded the broadest interpretation of the appended claims so as to encompass all equivalent apparatus and methods.

What is claimed is:

1. A kit for testing for formaldehyde and/or glutaraldehyde comprising:
    a first tablet containing a buffer and a strong acid;
    a second tablet containing benzoylacetone or its derivatives and ammonium acetate;
    a third tablet containing effervescing materials for effecting mixing of the materials within the first and second tablets with a test solution; and
    a color chart having a plurality of different intensity yellow color areas thereon, and indicia associated with each color area corresonding to a formaldehyde and/or glutaraldehyde concentration associated with that particular color.

2. A kit as recited in claim 1 wherein said third tablet contains sodium hydroxide and potassium carbonate.

3. A kit as recited in claim 1 wherein said third tablet contains sodium hydroxide and potassium carbonate.

4. A kit as recited in claim 1 wherein said second tablet is composed of approximately 5:0.040 parts of ammonium acetate to benzoylacetone or its derivatives, respectively.

5. A kit as recited in claim 1 wherein the first tablet contains citric acid and glycine hydrochloride.

6. A kit as recited in claim 5 wherein said second tablet is composed of approximately 5:0.040 parts of ammonium acetate to benzoylacetone or its derivatives, respectively.

7. A kit as recited in claim 6 wherein the first tablet contains approximately 19:2.8 parts of citric acid to glycine hydrochloride, respectively, and wherein the third tablet comprises approximately 14:5 parts of sodium hydroxide to potassium carbonate, respectively.

8. A kit for testing for formaldehyde and/or glutaraldehyde comprising:
    a first tablet comprising citric acid and glycine hydrochloride;
    a second tablet comprising benzoylacetone or its derivatives, and ammonium acetate;
    a third tablet comprising sodium hydroxide and potassium carbonate; and
    a color chart having a plurality of different intensity yellow color areas thereon, and indicia associated with each color area corresponding to a formaldehyde and/or glutaraldehyde concentration associated with that particular color.

9. A kit as recited in claim 8 wherein said second tablet is composed of approximately 5:0.040 parts of ammonium acetate to benzoylacetone or its derivatives, respectively.

10. A kit as recited in claim 9 wherein the first tablet contains approximately 19:2.8 parts of citric acid to glycine hydrochloride, respectively, and wherein the third tablet comprises approximately 14:5 parts of sodium hydroxide to potassium carbonate, respectively.

11. A method for testing for formaldehyde and/or glutaraldehyde utilizing a kit comprising: a first tablet containing a buffer and a strong acid; a second tablet containing color reagents including benzoylacetone or its derivatives and ammonium acetate; a third tablet containing effervescing materials, and a color chart having a plurality of different intensity yellow color areas thereon, and indicia associated with each color area corresponding to a formaldehyde and/or glutaraldehyde concentration associated with that particular color area; said method comprising the steps of:
    (a) dissolving the first and second tablets in a solution to be tested, the solution to be tested suspected of containing formaldehyde and/or glutaraldehyde;
    (b) adding the third tablet to the solution so as to effect effervescing of the materials to cause effective mixing thereof in the solution, and to cause a reaction between the formaldehyde and/or glurtaraldehyde, if present, and the color reagent to produce a yellow color; and
    (c) comparing the yellow color produced in step (b) to the yellow colored areas on the color chart to determine the approximate amount, if any, of formaldehyde and/or glutaraldehyde in the test solution.

12. A method as recited in claim 11 wherein the second tablet is composed of approximately 5:0.040 parts of ammonium acetate to benzoylacetone, respectively.

13. A method as recited in claim 11 wherein the materials in the first and third tablets are provided in proportion so that the pH during the practice of the color formation step (b) is maintained between about 4.5-6.

14. A method as recited in claim 11 wherein in the first tablet the buffer is citric acid and the strong acid is glycine hydrochloride, and wherein in the third tablet sodium hydroxide and potassium carbonate are present.

15. A method as recited in claim 14 wherein in the first tablet approximately 19:2.8 parts of citric acid to glycine hydrochloride are provided, and in the third tablet approximately 14:5 parts of sodium hydroxide to potassium carbonate are provided.

16. A method as recited in claim 15 wherein the second tablet is composed of approximately 5:0.040 parts of ammonium acetate to benzoylacetone, respectively.

17. A method for testing for formaldehyde and/or glutaraldehyde comprising the steps of:
    (a) forming a first solution containing benzoylacetone or its derivatives and ammonium acetate;
    (b) providing as part of the first solution materials which react to produce heat sufficient to cause a reaction between benzoylacetone or its derivatives and formaldehyde and/or glutaraldehyde to produce a yellow color, and for maintaining the pH of the first solution at about 4.5-6;
    (c) reacting the first solution with a second solution suspected to contain formaldehyde and/or glutaraldehyde to produce a yellow color if formaldehyde and/or glutaraldehyde are present; and
    (d) comparing the yellow color produced by the reaction of step (c) with a chart containing different yellow colors and formaldehyde and/or glutaraldehyde concentration levels corresponding to each of the different yellow colors on the chart.

18. A method as recited in claim 17 wherein the first and second solutions are the same solutions; that is a solution containing benzoylacetone or its derivatives comprises a solution suspected to contain formaldehyde and/or glutaraldehyde, and wherein steps (a)–(c) are practiced by: providing a plurality of tablets including a tablet containing benzoylacetone or its derivatives; mixing the tablet containing benzoylacetone or its derivatives with the second, test solution; and subsequently, to effect the practice of step (c), adding another table to the solution to effect effervescing thereof, and to facilitate the reaction of benzoylacetone or its derivatives with formaldehyde and/or glutaraldehyde.

19. A method of testing for formaldehyde and/or glutaraldehyde comprising the steps of:
   combining benzoylacetone or its derivatives and ammonium acetate, at a pH of about 4.5–6, with a test solution suspected to contain formaldehyde and/or glutaraldehyde to produce a yellow color if formaldehyde and/or glutaraldehyde are present; and
   comparing the yellow color produced to a chart containing different yellow colors and formaldehyde and/or glutaraldehyde concentration levels corresponding to each of the different yellow colors on the chart.

* * * * *